United States Patent [19]
Skarnes

[11] Patent Number: 5,767,336
[45] Date of Patent: Jun. 16, 1998

[54] GENE TRAP VECTORS COMPRISING A TYPE II TRANSMEMBRANE DOMAIN

[75] Inventor: William C. Skarnes, Edinburgh, United Kingdom

[73] Assignee: University of Edinburgh, Edinburgh, United Kingdom

[21] Appl. No.: 404,727

[22] Filed: Mar. 15, 1995

[30] Foreign Application Priority Data

Jan. 10, 1995 [GB] United Kingdom ............... 9500423

[51] Int. Cl.$^6$ ............................. C12N 5/00; C12N 15/00
[52] U.S. Cl. ..................... 800/2; 800/DIG. 1; 435/172.3; 435/325; 435/320.1
[58] Field of Search ..................... 435/320.1, 240.2, 435/325, 172.3; 800/2, DIG. 1

[56] References Cited

PUBLICATIONS

Moleuclar Cloning: A Laboratory Manuel 2nd ed, Sambrook et al., Cold Spring Harbor Laboratory Press Cold Spring Harbor, NY, 1989, pp. 1.13, 1.85–1.86 and 16.12.

Palmiter (1985) Cell 41, 343–345.

*Primary Examiner*—Deborah Crouch
*Attorney, Agent, or Firm*—Richard Aron Oswan

[57] ABSTRACT

Novel vectors are provided for capturing target genes, especially genes encoding membrane and secreted proteins as well as recombinant DNA molecules comprising sequences encoding genes so captured as well as the expression products of such genes.

The vectors comprise a component which upon insertion into a target eukaryotic gene produces a modified gene which on expression codes for a polypeptide having a portion of its amino acid sequence encoded by a nucleic acid sequence of the target eukaryotic gene and a portion of its amino acid sequence encoded by a nucleic acid sequence of the vector. The vector includes a sequence which confers on the polypeptide a property which is differentially associated with the presence in the target eukaryotic gene of a nucleic acid sequence coding for an amino acid sequence which results in the product of expressing the target eukaryotic gene being located in a predetermined spatial relationship with structural components of the host cell, e.g a secreted or membrane-spanning or trans-membrane protein.

16 Claims, 2 Drawing Sheets

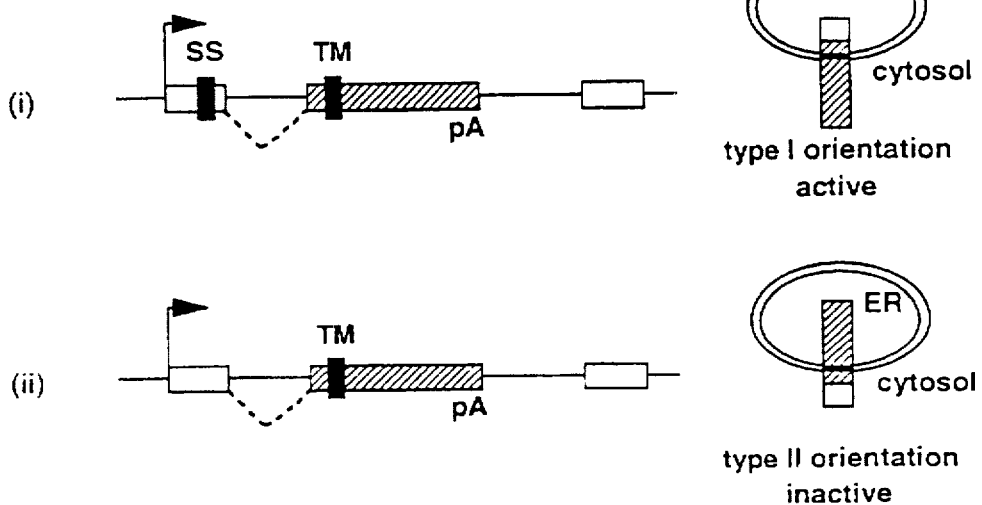

FIG. 1d

| | | G418^R colonies | | % βgal |
| --- | --- | --- | --- | --- |
| | | Expt 1 | 2 | positive |
| pGT1.8TM | [diagram: H — SA2 — TM — βgeo — C — S — H] | 33 | 250 | 20 |
| pGT1tm | [diagram: H — SA1 — TM — C — S — H] | 30 | - | 20 |
| pGT2tm | [diagram: H — SA2 — TM — C — S — H] | 21 | - | 20 |
| pGT3tm | [diagram: H — SA3 — TM — C — S — H] | 29 | - | 20 |
| pETtm | [diagram: H — TM — C — S — H] | - | 200 | 25 |

5,767,336

GENE TRAP VECTORS COMPRISING A TYPE II TRANSMEMBRANE DOMAIN

This invention relates to novel vectors and use thereof for capturing target genes, especially genes encoding membrane and secreted proteins. The invention further provides recombinant DNA molecules comprising sequences coding for genes so captured as well as the expression products of such genes themselves.

DESCRIPTION OF PRIOR ART

Vectors known as "gene trap vectors" have been developed which allow the isolation of coding sequences associated with eukaryotic genes (Skarnes, 1990). Typically such vectors possess structural components which facilitate isolation of vector sequences inserted into transcription units so as to form recombinant sequences and other elements which allow the resulting recombinant sequences to be identified and/or characterised. Thus, for example, the known vectors may contain sequences which are commonly associated with eukaryotic structural genes, such as for example splice acceptor sites which occur at the 5' end of all exons, and polyadenylation sites which normally follow the final exon. If the vector inserts within an intron in the correct orientation, the splice acceptor and polyadenylation sites are utilized to generate a fusion RNA transcript that contains a portion of the target gene spliced to reporter gene sequences of the vector. Other vectors with similar function do not rely on splicing, but instead recombine within coding sequences of the target gene simply as a result of random recombinational events.

Each insertion event that activates expression of the reporter gene therefore represent insertions that disrupt the normal coding sequences of the target gene to create a mutation. Furthermore, expression of the reporter gene comes under the regulatory control of the target gene and thus reporter gene expression should reflect the expression pattern of the target gene. Lastly, a portion of the target gene contained in the RNA fusion transcript may be cloned directly from the fusion transcript or from genomic DNA upstream of the site of insertion.

Thus, for example, gene trapping in mouse embryonic stem (ES) cells has hitherto offered a rapid, but essentially random method to identify and simultaneously mutate genes expressed during mouse development (Skarnes, 1990). There is however a need to identify and/or isolate target eukaryotic genes on the basis of various selection criteria rather than randomly. A particular class of genes of interest are ones which are expressed as proteins which adopt a particular spatial relationship with cellular structural components, in particular secreted and membrane-spanning proteins.

Secreted proteins are generally but not exclusively characterised in that they contain an N-terminal extension (or "signal sequence") of roughly 18 to 25 hydrophobic amino acids. This signal sequence directs the translation product to the secretory pathway such that the polypeptide translocates across a cell membrane for export from the cell. For the most part, the signal sequence is proteolytically cleaved from the polypeptide during the secretion process whereby the final secreted product lacks this sequence. Secreted proteins in this class include, for instance, polypeptide hormones and cytokines.

Membrane-spanning proteins generally contain, in addition to a signal sequence, one or more hydrophobic sequences, often of similar size, downstream of the signal sequence. The transmembrane domain prevents further translocation of the polypeptide, so resulting in the production of a protein that spans the membrane. Transmembrane proteins in this class include, for instance, receptors for polypeptide hormones and receptors for cytokines.

Bacterial reporter genes such as β-galactosidase (β-gal) and βgeo, a fusion polypeptide that possesses both βgal and neomycin (neo) phosphotransferase activities, lack signal sequences and transmembrane sequences. If a signal sequence is affixed to the N-terminus of β-gal or βgeo the protein product enters the secretory pathway. This, however, may not result in export of an active protein from the cell, and it is thought that bacterial reporters are often incompatible with eukaryotic secretion pathways.

Thus, integration of a β-gal or βgeo reporter into a resident gene encoding a signal sequence, such that the fusion gene encodes a hybrid polypeptide that contains a N-terminal signal sequence derived from the resident gene fused to the reporter, can fail to give rise to functional βgal activity. This is because the reporter gene product enters the secretory pathway where it is inactivated. For this reason conventional gene trap vectors usually fail to permit the isolation of insertions into genes encoding secreted proteins.

We have now developed a strategy which solves the problems outlined above and which in its more specific aspects is based on gene trap protocols.

STATEMENTS OF INVENTION

According to a first aspect of the present invention, there are provided vectors comprising a component which upon insertion into a target eukaryotic gene produces a modified gene which on expression codes for a polypeptide having (1) a portion of its amino acid sequence encoded by a nucleic acid sequence of the target eukaryotic gene and (2) a portion of its amino acid sequence encoded by a nucleic acid sequence of the vector, characterised in that the vector includes a sequence which confers on the polypeptide a property which is differentially associated with the presence in the target eukaryotic gene of a nucleic acid sequence coding for an amino acid sequence which results in the product of expressing the target eukaryotic gene being located in a predetermined spatial relationship with structural components of the host cell.

A particularly useful class of vectors according to the invention are ones wherein the vector includes one or more sequences which confer or confers on the polypeptide a property which is differentially associated with the presence in the target eukaryotic gene of a signal sequence associated with a secreted or membrane-spanning protein. The aforementioned sequences can, for example comprise at least a portion of a membrane-associated protein. In this embodiment, the protein product encoded by a reporter gene element of the vector can be forced to adopt, on integration into a target gene, one of two configurations, depending on whether or not the target gene includes a signal sequence associated with a secreted or membrane-spanning protein. Thus for example, if the target gene does code for a secreted or membrane-spanning protein the membrane-associated protein element of the vector sequence can cause a reporter gene product to adopt a configuration in relation to cell components such that the reporter gene product is activated and produces a detectable signal. Alternatively if the vector is incorporated into target gene which does not code for a secreted or membrane-spanning protein, the membrane-associated protein element of the vector sequence will cause reporter gene product to adopt a configuration in relation to cell components such that the reporter gene product is not activated and consequently will not produces a detectable signal. The aforementioned membrane associated protein can conveniently comprise a trans-membrane protein.

Thus according to a further and more specific aspect, the invention provides a vector comprising a component which upon insertion into a target eukaryotic gene produces a modified gene which on expression codes for a polypeptide having (1) a portion of its amino acid sequence encoded by a nucleic acid sequence of the target eukaryotic gene and (2) a portion of its amino acid sequence encoded by a nucleic acid sequence of the vector, characterised in that the vector includes a reporter gene and a sequence encoding a transmembrane domain of a transmembrane protein (particularly a transmembrane domain placed N-terminally to the reporter), each mutually arranged so that on expression of the modified gene, detection of reporter polypeptide activity is dependent upon whether the target eukaryotic gene codes for a secreted protein having a signal sequence or a non-secreted protein.

Such vectors are preferably characterised in that the vector includes a reporter gene and a sequence encoding a transmembrane domain (particularly a transmembrane domain placed N-terminally to the reporter) of a transmembrane protein arranged so that on expression of the modified gene, reporter polypeptide activity is detectable if the target eukaryotic gene codes for a secreted protein having a signal sequence, and is substantially undetectable if the target eukaryotic gene codes for a non-secreted protein.

The vectors of the invention preferably include a nucleic acid sequence which facilitates insertion of said component into the target eukaryotic gene. These sequences may for example be (a) sequences associated with elimination of intron sequences from mRNA, such as, for example splice acceptor sequences, or (b) polyadenylation signal sequences. Alternatively, the vector may lack a splice acceptor sequence and thus rely on insertions directly into the coding sequences of genes.

Thus more specifically the invention provides a vector comprising a nucleic acid sequence facilitating insertion of components of the vector into a target eukaryotic gene so as to produce a modified gene which on expression codes for a polypeptide having (1) a portion of its amino acid sequence encoded by a nucleic acid sequence of the target eukaryotic gene and (2) a portion of its amino acid sequence encoded by a nucleic acid sequence of the vector, characterised in that the vector includes a sequence which confers on the polypeptide a property which is differentially associated with the presence in the target eukaryotic gene of a nucleic acid sequence coding for an amino acid sequence which results in the product of expressing the target eukaryotic gene being located in a predetermined spatial relationship with structural components of the host cell.

The vectors according to the invention preferably include a nucleic acid marker sequence allowing selection and/or identification of cells transformed as a result of components of the vector having been inserted into the target eukaryotic gene. Examples of such marker sequences are ones which result in transformed cells being resistant to an antibiotic, for example G418, or having a varied degree of dependence on a growth factor or nutrient.

One example of a terminal transmembrane domain which can be employed in the context of the above embodiments is the CD4 transmembrane domain. Preferably the transmembrane domain element of the vector contains additional flanking sequences. Thus where a CD4 transmembrane domain is used, the vector will contain additional CD4 sequences so as to ensure correct operation of the transmembrane domain.

Alternatively or additionally, the vectors according to the invention may include a reporter gene, i.e. they convey a property on transformed cells in the form of a phenotype allowing selection and/or identification of cells transformed as a result of components of the vector having been inserted into the target eukaryotic gene. The phenotype may for example be the production of a detectable enzyme such as β-galactosidase.

As indicated, a particularly useful class of vectors according to the invention are ones wherein said amino acid sequence which results in the product of expressing the target eukaryotic gene being located in a predetermined spatial relationship with structural components of the host cell is a signal sequence, especially one associated with secretion of the target gene product from the cell.

The invention further provides a method of detecting and/or isolating a target eukaryotic gene encoding a protein which is located in a predetermined spatial relationship with structural components of the host cell which comprises transforming a cell utilising a vector as defined above and detecting the transformed cell by assaying for said property which is differentially associated with the presence in the target eukaryotic gene of a nucleic acid sequence coding for an amino acid sequence which results in the product of expressing the target eukaryotic gene being located in a predetermined spatial relationship with structural components of the host cell.

Eukaryotic genes isolated by this procedure form a further part of the invention.

The vectors and method of the invention have allowed us to pre-screen mouse embryonic stem cells for insertional mutations in genes encoding secreted and membrane-spanning proteins.

DESCRIPTION OF FIGURES

The invention will now be described in more detail by way of example with particular reference to the accompanying Figure:

FIG. 1a shows the vectors designed to express CD4/βgeo fusion proteins and summarises the results of transient transfection experiments.

FIG. 1b shows the design of gene trap vectors (pSAβgeo and pGT1.8geo) and the secretory trap vector (pGT1.8TM) and their relative efficiency in stable transfections of ES cells.

FIG. 1c depicts our model for the selection activation of βgal in the secretory trap vector.

FIG. 1d shows the relative efficiency of secretory trap vectors designed to capture each of the three reading frames and the exon trap design.

DESCRIPTION OF SPECIFIC EMBODIMENTS

In these experiments, modified gene trap vectors (which we have termed "secretory trap") were developed which rely on capturing the N-terminal signal sequence of an endogenous gene to generate an active β-galactosidase fusion protein. Using the prototype vector pGT1.8TM (FIG. 1b), insertions were found in the extracellular domains of a novel cadherin, an unc6- related laminin, the sek receptor tyrosine kinase and two receptor-linked protein tyrosine phosphatases, LAR and PTPκ, thus confirming the selective property of the secretory trap vector to detect insertional mutations in genes encoding transmembrane and secreted protein products.

The secretory trap strategy was developed starting from lacZ-based gene trap vectors (Gossler et al., 1989; Brenner et al., 1989; Kerr et al., 1989; Friedrich & Soriano, 1991; Skarnes, Auerbach & Joyner, 1992). These vectors create N-terminal β-galactosidase (βgal) fusion products which localise to different compartments of the cell, presumably reflecting the acquisition of endogenous protein sequences that act as sorting signals (Skarnes et al., 1992; Burns et al., 1994).

To test if βgal fusions that contain an N-terminal signal sequence could be identified by their subcellular distribution, vectors were constructed to express portions of the CD4 type I membrane protein (Clark et al., 1987) fused to βgeo, a chimeric protein that possesses both βgal and neomycin phosphotransferase activities (Friedrich & Soriano, 1991) (FIG. 1a).

1. Subcellular localization of CD4/βgeo fusion products

Referring to FIG. 1a, the βgeo reporter was obtained by replacing the ClaI (unique in lacZ)/SphI (unique in neo) fragment of the gene trap vector pGT1.8 with the ClaI/SphI fragment of pSAβgeo (Friedrich & Soriano, 1991). pGT1.8 is a derivative of pGT4.5 (Gossler et al., 1989) where the 3' En2 sequences were replaced with the 0.2 kb BclI/BamHI SV40 polyA signal. The parental vector pActβgeo contains the 0.5 kb human β-actin promoter (Joyner, Skarnes & Rossant, 1989) linked to the βgeo/SV40 polyA cassette. The start of βgeo translation was engineered to contain a Kozak consensus sequence with unique SalI and NruI sites on either side for generating subsequent fusions (SDK oligo from S. Darling). SalI sites were placed at each end of a BalI fragment containing the entire coding region of the rat CD4 cDNA (Clark et al., 1987) A 0.45 kb SalI/KpnI fragment containing the N-terminus of CD4 or a 1.4 kb SalI/NdeI fragment containing the entire CD4 coding region was cloned into SalI/NruI digested pActβgeo to generate pActSSβgeo and pActSSTMβgeo, respectively. The results of transient transfection experiments are summarised in the right-hand column of FIG. 1a.

The human β-actin (ACT) promoter was used to drive expression of βgeo alone (pActβgeo), fused in frame to the signal sequence (SS) of CD4 (pActSSβgeo), or fused to the SS and transmembrane (TM) domain of CD4 (pActSSTMβgeo). $10^7$ CGR8 ES cells (a feeder-independent cell line established from the 129/Ola strain by J. Nichols and A. Smith according to published protocols) (Stewart, 1993) were electroporated 250 μF/250V, BioRad Genepulser) (Gossler et al., 1989) in a volume of 0.8 ml PBS with 100 μg uncut plasmid DNA and cultured for 36 hrs. Cells grown on gelatinized coverslips were assayed for βgal activity using X-gal (Beddington et al., 1989) and βgeo protein was detected by immunofluorescence (+/−0.5% NP-40) using polyclonal rabbit a-βgal antiserum (a gift from J. Price) and FITC-conjugated donkey a-rabbit IgG (Jackson ImmunoResearch) (Hurtely, 1993). Photomicrographs showed that ES cells were transiently transfected with pActβgeo; pActSSβgeo and pActSSTMβgeo and assayed for βgal activity (bright field) and protein (dark field).

βgeo alone is evenly distributed in the cytoplasm of cells. βgeo fused to the signal sequence of CD4 (pActSSβgeo) accumulated in the endoplasmic reticulum (ER) but lacked βgal activity. Therefore, translocation of βgeo into the lumen of the ER appears to abolish βgal enzyme function. βgal activity was restored by including the transmembrane domain of CD4 (pActSSTMβgeo), presumably by keeping βgal in the cytosol. Active protein was localized in the ER and in multiple cytoplasmic inclusions, a pattern only rarely observed in ES colonies obtained with the conventional gene trap vector probably because insertions downstream of both a signal sequence and transmembrane domain of genes encoding membrane spanning proteins are infrequent. Therefore, to identify insertions in both secreted and type I membrane proteins our gene trap vector pGT1.8geo was modified to include the transmembrane domain of CD4 upstream of βgeo (FIG. 1b).

2. Construction and relative efficiency of gene trap and secretory trap vectors

The gene trap and secretory trap vectors used in this study contain the βgeo reporter derived from pSAβgeo (Friedrich & Soriano, 1991). Referring to FIG. 1b, pSAβgeo contains the minimal adenovirus type 2 major late splice acceptor (SA; open box, intron; shaded box, exon) and the bovine growth hormone polyadenylation signal. The mutation in neo (*) present in pSAβgeo was corrected in our vectors by replacement of the ClaI (C)/Sph I (S) fragment of βgeo. pGT1.8geo and pGT1.8TM contain the mouse En-2 splice acceptor (Gossler et al., 1989) and SV40 polyadenylation signal but lack a translation initiation signal (ATG). The secretory trap vector pGT1.8TM includes the 0.7 kb PstI/NdeI fragment of CD4 containing the transmembrane domain inserted in-frame with βgeo in pGT1.8geo.

Referring to FIG. 1d, vectors in each reading frame (pGT1tm to 3tm) were constructed by ExoIII deletion of all but 30 bp of En-2 exon sequences followed by the insertion of Bgl II linkers. The exon trap vector (pETtm) was made by removing the En-2 splice acceptor from pGT1.8TM.

The relative efficiencies in ES cells of the gene trap and secretory trap vectors are given in FIG. 1b. Vectors were linearised prior to electroporation at either the Sca I (Sc) site in the plasmid backbone (represented by the line) of pSAβgeo or at the Hind III (H) site at the 5' end of the En-2 intron. CGR8 ES cells were electroporated (3 μF/800V) with 150 μg linearised plasmid DNA. $5 \times 10^6$ cells were plated on 10 cm dishes and colonies were selected in 200 μg/ml Geneticin (GibCo). The number of G418-resistant colonies obtained in two electroporation experiments (Expt 1: $5 \times 10^7$ cells; Expt 2: $10^8$ cells) and the proportion that express detectable βgal activity is indicated on the right.

In a pilot experiment, the relative efficiency of our gene trap vector was compared to the original pSAβgeo following electroporation into ES cells. Although pSAβgeo contains a start of translation which is absent in our vectors, fewer G418-resistant colonies were obtained with pSAβgeo than with pGT1.8geo. More importantly, nearly all the colonies derived with pSAβgeo showed high levels of βgal activity, whereas our vector showed a broad range of staining intensities and a greater proportion of βgal negative colonies. Sequence analysis of the pSAβgeo vector revealed a point mutation in neo known to reduce its enzyme activity (Yenofsky, Fine & Pellow, 1991). Therefore, the pSAβgeo vector appears to pre-select for genes expressed at high levels and correction of the neo mutation in our vectors now allows us to access genes expressed at low levels (see below).

Approximately half of the pGT1.8geo colonies express detectable βgal activity and show various subcellular patterns of βgal staining observed previously. In contrast, only 20% of the pGT1.8TM colonies express βgal activity and all display the "secretory" pattern of βgeo activity characteristic of the pActSSTMβgeo fusion. Stable cell lines transfected with pGT1.8TM in most cases showed detectable βgal activity in undifferentiated ES cells however, we occaisionally found ES cell lines that exhibited detectable βgal activity only in a subset of differentiated cell types. The reduction in the proportion of βgal-positive colonies and the singular pattern of βgal staining observed with the secretory trap vector suggested that βgal activity is retained only in fusions that contain an N-terminal signal sequence and that βgal activity, but not neo, activity is lost in fusions with proteins that do not possess a signal sequence.

3. Model for the selective activation of βgal in fusions that acquire a signal sequence From our data, we propose that in the absence of cleavable N-terminal signal sequence, the fusion protein behaves as a type II membrane protein (High, 1992), placing βgeo in the ER lumen where the βgal enzyme is inactive (FIG. 1c). To confirm this, several βgal-negative cell lines were isolated and analysed by immunofluorescence. βgal-negative cells lines were identified from immunodotblots of whole cell lysates using a-βgal antibodies and the ECL detection system (Amersham). From a screen of 48 colonies, three βgal-negative cell lines were recovered and analysed by immunofluorescence. In these lines, the fusion protein was detected on the surface of cells in the absence of detergent permeabilization, indicating a type II orientation of the βgeo fusion protein.

In contrast, detergent permeabilization was essential to detect the fusion protein in βgal-positive cell lines, as would be expected for type I membrane proteins. Thus, in fusions that contain a signal sequence, the transmembrane domain in the vector acts to prevent βgeo from entering the ER lumen, thereby preserving its cytosolic enzyme activity. This dependence of enzyme activity on acquiring an endogenous signal sequence provides a simple screen for insertions into genes that encode N-terminal signal sequences.

A model for the observed selective activation of βgal in the secretory trap vector is presented in FIG. 1c. Insertion of pGT1.8TM (hatched box) in genes that contain a signal sequence produce fusion proteins that are inserted in the membrane of the endoplasmic reticulum in a type I configuration. The transmembrane domain of the vector retains βgal in the cytosol where it remains active. Insertion of the vector in genes that lack a signal sequence produce fusion proteins with an internal TM domain. In these fusions, the transmembrane domain acts as a signal anchor sequence (High, 1992) to place βgeo in a type II orientation, exposing βgeo to the lumen of the ER where βgal activity is lost. Final proof for this model has come from cloning several genes associated with several secretory trap insertions.

4. Molecular analysis of trapped genes

Northern blot analysis detected a unique-sized βgeo fusion transcript in each cell line which did not hybridize to intron sequences of the vector (data not shown). A Northern blot of 15 µg ES cell RNA was hybridised with lacZ gene and reprobed with a RACE cDNA fragment cloned from the ST534 (LAR) insertion. The pGT1.8TM vector is predicted to contribute 5 kb to the size of the fusion transcript.

5' RACE (rapid amplification of cDNA ends) (Frohman, Dush & Martin, 1988) was used to clone a portion of the endogenous gene associated with six properly spliced secretory trap insertions (Table I). Several modifications were incorporated into the 5' RACE procedure used previously (Skarnes, Auerbach & Joyner, 1992): 1) microdialysis (0.025 micron filters, Millipore) was used in place of ethanol precipitations, 2) nested PCR (30 cycles each) was carried out using an anchor primer (5'-GGTTGTGAGCTC TTCTAGATGG) (SEQ ID NO: 1) and a primer specific to CD4 (5'-AGTAGACTTCTGCACAGACACC) (SEQ ID NO: 2) followed by size selection on agarose gels and a second round of PCR with the anchor and the En-2 256 primer and 3) chromospin 400 columns (Clontech) were used to size select XbaI/Kpn-digested PCR products prior to cloning.

At least two independent RACE cDNAs were cloned from each cell line. The cDNAs obtained from all cell lines except ST514 detected both the fusion transcript and an endogenous transcript common to all cell lines as shown for the ST534 probe. The ST514 insertion illustrates that genes expressed a very low levels in ES cells can be trapped. In ST514 cultures, βgal activity was observed only in a few differentiated cells and accordingly neither the fusion nor the endogenous transcripts could be detected on the Northern blot.

Sequence analysis of the RACE cDNAs in all cases showed the proper use of the splice acceptor and a single open reading frame in-frame with βgeo. One of the insertions occurred in a secreted laminin homologous to the unc-6 gene of C. elegans (Ishii et al., 1992) also recently cloned in chick (Serafini et al., 1994). The remaining five insertions interrupted the extracellular domains of membrane spanning proteins: a novel cadherin most closely related to the fat tumor suppressor gene of Drosophila (Mahoney et al., 1991), the sek receptor tyrosine kinase (Gilardi-Hebenstreit et al., 1992), the receptor-linked protein tyrosine phosphatase PTP__(Jiang et al., 1993), and two independent insertions in a second receptor-linked phosphatase LAR (Streuli et al., 1988). These results support the prediction that βgal activity is dependent on acquiring an N-terminal signal sequence from the endogenous gene at the site of insertion.

5. Target genes biased by secretory trap vector design

Based on the first six genes identified, the secretory trap approach appears to favor insertions in large transmembrane receptors. The requirement for gene trap vectors to insert in introns of genes probably contributes in large part to this bias, i.e., transcription units composed of large intronic regions will be more likely targets. To increase the number of genes accesible to the secretory trap, constructs have been engineered in each of the three possible reading frames. Each reading frame is predicted to target a similar number but different set of genes. Furthermore, an exon trap vector was constructed by removing the splice acceptor, thus, activation of the βgeo reporter now depends on insertions into exons of genes. The exon trap vector should be useful in detecting small transcription units composed of few or no introns.

The relative efficiencies of secretory trap vectors engineered in all three reading frames and the exon trap vector are given in FIG. 1d. Electroporations of CGR8 ES cells were carried out as described above (Expt 1: $2 \times 10^7$ cells; Expt 2: $10^8$ cells). Vectors in each reading frame were equally as efficient as the original secretory trap vector with a similar proportion of colonies express detectable βgal activity. Unexpectedly, the exon trap design yielded only a small reduction in the number of G418-resistant colonies with a slight increase in the propotion of βgal positive colonies. One exon trap vector design was previously shown to be substantially less efficient in trapping genes (Friedrich & Soriano, 1991), in keeping with the idea that introns provide a much larger target than exons. Our results now cast doubt on this assumption, however, further study will be needed to resolve this apparent discrepancy in exon trapping efficiencies. Furthermore, cloning genes associated with each vector will be required to determine if these vectors do indeed target different sets of genes.

6. Reporter gene activity accurately reflects endogenous gene expression

Chimeric embryos and germline mice were generated by injection of C57Bl/6 blastocysts (Skarnes, Auerbach & Joyner, 1992). Embryos at the appropriate stages were dissected, fixed and stained with X-gal as described (Beddington et al., 1989). Heterozygous 9.5 d embryos: a, ST534 (LAR), dorsal view showing widespread, low level βgal expression; b, ST531 (PTPκ), lateral view showing high expression in paraxial mesoderm and somites; c, ST497 (sek), dorsal view showing characteristic sek expression in the forebrain, rhombomeres 3 and 5 of the hindbrain, lateral and paraxial mesoderm and somites (Nieto et al., 1992). (d to e) ST514 chimeric 10.5 d embryo: d, lateral view and e, cross-section showing expression in ventral spinal cord, floorplate and dermamyotome of somites.

The pattern of βgal expression in embryos derived from insertions in the sek (ST497) and netrin-1 (ST514) genes was very similar to published RNA in situ results for the mouse sek (Nieto et al., 1992) and chick netrin (Kennedy et al., 1994) genes, providing further evidence that gene trap vectors accurately report the pattern of endogenous gene expression (Skarnes, Auerbach & Joyner, 1992). Both insertions in LAR (ST484, 534) exhibited weak, widespread expression in 8.5 d embryos. The insertion in PTPκ (ST531) showed βgal expression in endoderm and paraxial mesoderm, highest in newly condensing somites. βgal expression in tissues of adult mice carrying insertions in LAR and PTPκ correlated well with known sites of mRNA expression (Jiang et al., 1993; Longo et al., 1993). Highest levels of βgal activity were found in the lung, mammary gland and brain of ST534 (LAR) mice and in the kidney, brain and liver of ST531 (PTPκ) mice (data not shown).

7. The secretory trap vector effectively disrupts the gene at the site of insertion Following germline transmission of the PTPκ and LAR insertions, breeding analysis showed that mice homozygous for either insertion are viable and fertile. To confirm that the LAR and PTPκ genes were effectively disrupted, Northern blots of RNA from wild-type and homozygous adult tissues were probed with cDNAs from regions downstream of each insertion site. For both mutations, full-length transcripts were not detected in homozygous animals.

Because secretory trap insertions generate fusions that in some cases will contain a large portion of the extracellular domain of the target gene, the production of both loss of function and gain of function (i.e., dominant-negative) mutations are possible. However, since the βgeo fusions with LAR and PTPκ include less than 300 amino acids of the extracellular domains of these proteins, these insertions likely represent null mutations. LAR and PTPκ are members of an ever-increasing family of receptor PTP genes (Saito, 1993).

prove advantageous in determining their role during embryogenesis.

8. Summary

It will be appreciated that in this invention we have shown that the βgeo reporter gene can be modified to contain an N-terminal transmembrane domain. Integration into an endogenous gene encoding an N-terminal signal sequence produces a fusion protein that assumes a type I configuration, keeping βgal in the cytosol where it retains functional enzyme activity (see FIG. 1c (i)).

Conversely, if the modified reporter integrates into a gene that does not encode a signal sequence, the hydrophobic transmembrane domain itself is now recognised by the cell as a signal sequence to place the fusion protein in a type II orientation whereupon the βgal enzyme is inactivated (see FIG. 1c (ii)).

Therefore, a construct in which βgal or βgeo is prefixed by an N-terminal transmembrane domain has a unique property. If the construct integrates into a 'secretory' gene encoding a signal sequence, the βgal remains active. If it integrates into a non-secretory gene, βgal activity is blocked. This permits integrations into secretory genes to be selected by simple selection for reporter gene activity.

Not all transmembrane domains may function as described above. Constructs comprising only the isolated transmembrane domain of CD4, for instance, failed to show the selective properties characteristic of pGT1.8TM and its derivatives. Therefore, it may be necessary to use a more extensive segment of CD4, encompassing the transmembrane domain and containing additional flanking CD4 sequences, to permit correct operation of the transmembrane domain. The selection of the sequences encompassing the transmembrane domain thus may be a critical feature of the present invention.

TABLE 1

Identification of the endogenous gene associated with six secretory trap insertions.

| cell line | βgal expression[1] ES | diff | transcript size (kb)[2] fusion | endogenous | gene[3] | phenotype[4] | (wt:het:hom) |
|---|---|---|---|---|---|---|---|
| 484 | + | + | 7.5 | 7.5 | LAR (604) | NA | |
| 497 | + | +/− | 6.5 | 7 | sek (439) | ? | |
| 514 | − | +/− | ND | ND | netrin (404) | ? | |
| 519 | − | +/− | >12 | >12 | novel cadherin | NA | |
| 531 | − | +/− | 6.1 | 5.3 | PTP$_κ$ (288) | viable | (36:57:27) |
| 534 | + | + | 6.0 | 7.5 | LAR (228) | viable | (36:79:25) |

[1]based on X-gal staining of ES cell cultures that contain a subset of spontaneously differentiated (diff) cell types,
(+/−) indicates expression in a subset of differentiated cell types.
[2]transcript sizes were determined from Northern blots (FIG. 4 and data not shown).
N.D., not detected.
[3]numbers in parentheses indicate the insertion site within the endogenous based on the amino acid sequence of rat LAR (AC L11586), mouse sek (AC S51422), chick netrin 1 (AC L34549), and mouse PTP$_κ$ (AC L10106). The Genbank accession number for the novel cadherin is (to be submitted).
[4]based on the recovery of homozyogous animals at weaning age in litters from heterozygous intercrosses.
(?)phenotype unknown, breeding in progress.
NA, not applicable, insertion not yet in germline.

The absence of overt phenotypes in LAR and PTPκ mutant mice is likely due to functional overlap between gene family members, as has been observed with targeted mutations in multiple members of the myogenic and Src-family genes (Rudnicki et al., 1993; Stein, Vogel & Soriano, 1994; Lowell, Soriano & Varmus, 1994). In this regard, the preferential recovery of secretory insertions in multiple members of a given family of cell surface proteins (e.g., receptor PTPs) and the production of compound mutant mice may

REFERENCES

Beddington, R. S. P et al. *Development* 106, 37–46 (1989).
Brenner, D. G., Lin-Chao, S. & Cohen, S. N. *Proc. Nat Acad. Sci. USA* 86, 5517–5521 (1989).
Burns, N. et al. *Genes Dev.* 8, 1087–1105 (1994).
Clark, S. J. et al., *Proc. Nat. Acad. Sci. USA* 84, 1649–1653 (1987).
Friedrich, G. & Soriano P. *Genes Dev.* 5, 1513–1523 (1991).

Frohman, M. A., Dush, M. K., & Martin, G. *Proc. Nat. Acad. Sci. USA* 85, 8998–9002 (1988).

Gilardi-Hebenstreit, P. et al. *Oncogene* 7, 2499–2506 (1992).

Gossler, A., Joyner, A. L., Rossant J. & Skarnes, W. C. *Science* 244, 463–465 (1989).

High, S. *Bioessays* 14, 535–540 (1992).

Hurtley, S. M. *J. Cell Sci.* 106, 649–655 (1993).

Ishii, N. et al., *Neuron* 9, 873–881 (1992).

Jiang, Y. -P. et al. *Mol. Cell. Biol.* 13, 2942–2951 (1993).

Joyner A. L., Skarnes, W. C. & Rossant, J. *Nature* 338, 153–156 (1989).

Kennedy, T. E. et al. *Cell* 78, 425–435 (1994).

Kerr, W. G., Nolan, G. P., Serafini, A. T. & Herzenberg, L. A. *Cold Spring Harbor Symp. Quant. Biol.* 54, 767–776 (1989).

Longo, F. M et al. *J. Biol. Chem.* 268, 26503–26511 (1993).

Lowell, C. A., Soriano, P. & Varmus, H. *Genes & Dev.* 8, 387–398 (1994).

Mahoney, P. A. et al. *Cell* 67, 853–868 (1991).

Nieto, M. et al. *Development* 116, 1137–1150 (1992).

Rudnicki, M. A. et al. *Cell* 75, 1351–1359 (1993).

Saito, H. *Semin. Cell Biol.* 4, 379–387 (1993).

Serafini, T. et al. *Cell* 78, 409–424 (1994).

Skarnes, W. C. *Biotechnology.* 8, 827–831 (1990).

Skarnes, W. C., Auerbach, A. & Joyner, A. L. *Genes Dev.* 6, 903–918 (1992).

Stein, P. L., Vogel, H. & Soriano, P. *Genes & Dev.* 8, 1999–2007 (1994).

Stewart, C. L. *Methds Enzymol.* 225, 823–855 (1993).

Streuli, M. et al. *J. Exp. Med.* 168, 1523–1530 (1988).

Yenofsky, R. L., Fine, M. & Pellow, J. W. *Proc. Nat. Acad. Sci. USA* 87, 3435–3439 (1991).

I claim:

1. A vector comprising a DNA sequence encoding a reporter gene and a type II transmembrane domain positioned N-terminally to the reporter gene, wherein upon transfer into a cell and stable integration of the DNA sequence into a target gene, expression of the reporter gene is detectable if the target gene encodes a secreted or membrane-spanning protein having a signal sequence and is undetectable if the target gene codes for a non-secreted, non-membrane spanning protein not having a signal sequence.

2. The vector according to claim 1, wherein the vector further comprises a gene encoding a selectable marker.

3. The vector according to claim 2, wherein the selectable marker is for antibiotic resistance.

4. The vector according to claim 3, wherein the antibiotic resistance is to G418.

5. The vector according to claim 2, wherein the selectable marker is dependence on nutrient.

6. The vector according to claim 2, wherein the selectable marker is dependence on a growth factor.

7. The vector according to claim 1, wherein the reporter gene encodes an enzymatic activity.

8. The vector according to claim 1, wherein the reporter gene encodes β-galactosidase.

9. A method of identifying a target eukaryotic gene, the method comprising the steps:
  a) introducing into a cell in vitro a vector comprising a DNA sequence encoding a reporter gene and a type II transmembrane domain positioned N-terminally to the reporter gene, wherein upon transfer into the cell, the DNA sequence stably integrates into a target gene;
  b) incubating the cell in vitro under conditions wherein the reporter gene is expressed by the cells or descendant of the cell;

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:1:

GGTTGTGAGC TCTTCTAGAT GG    22

( 2 ) INFORMATION FOR SEQ ID NO:2:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:2:

AGTAGACTTC TGCACAGACA CC    22 c) determining that the target gene encodes a secreted or membrane-spanning protein having a signal sequence by the detection of reporter gene expression or determining that the target gene encodes a non-secreted, non-membrane spanning protein not having a signal sequence by the undetectable expression of the reporter gene; and d) identifying the target gene.

10. A method of identifying a target eukaryotic gene, the method comprising the steps:

a) introducing into a cell in vitro a vector comprising a DNA sequence encoding β-galactosidase and a type II transmembrane domain positioned N-terminally to the β-galactosidase coding region of the DNA sequence, wherein upon transfer into the cell the DNA sequence stably integrates into a target gene;

b) incubating the cell in vitro under conditions wherein β-galactosidase is expressed by the cell or descendant of the cell;

c) determining that the target gene encodes a secreted or membrane-spanning protein having a signal sequence by the detection of β-galactosidase expression or determining that the target gene encodes a non-secreted, non-membrane spanning protein not having a signal sequence by the undetectable β-galactosidase expression; and d) identifying the target gene.

11. An isolated cell comprising a vector according to claim 1, wherein the DNA sequence is stably integrated into a gene of the cell, and wherein expression of the reporter gene permits identifying genes which encode a secreted or membrane-spanning protein having a signal sequence and genes which encode a non-secreted, non-membrane spanning protein not having a signal sequence.

12. An isolated cell comprising a vector according to claim 8, wherein the DNA sequence is stably integrated into a gene of the cell, and expression of β-galactosidase permits identifying genes which encode a secreted or membrane-spanning protein having a signal sequence and genes which encode a non-secreted, non-membrane spanning protein not having a signal sequence.

13. An isolated pluripotent cell comprising a vector according to claim 1, wherein the DNA sequence is stably integrated into a gene of the cell, and expression of the reporter gene permits identifying genes which encode a secreted or membrane-spanning protein having a signal sequence and genes which encode a non-secreted, non-membrane spanning protein not having a signal sequence.

14. An isolated pluripotent cell comprising a vector according to claim 8, wherein the DNA sequence is stably integrated into a gene of the cell, and expression of β-galactosidase permits identifying genes which encode a secreted or membrane-spanning protein having a signal sequence and genes which encode a non-secreted, non-membrane spanning protein not having a signal sequence.

15. A transgenic mouse comprising a vector according to claim 1, wherein the DNA sequence is stably integrated into a gene of the mouse, and expression of the reporter gene permits identifying of genes which encode a secreted or membrane-spanning protein having a signal sequence and genes which encode a non-secreted, non-membrane spanning protein not having a signal sequence.

16. A transgenic mouse comprising a vector according to claim 8, wherein the DNA sequence is stably integrated into a gene of the mouse, and expression of β-galactosidase permits identifying genes which encode a secreted or membrane-spanning protein having a signal sequence and genes which encode a non-secreted, non-membrane spanning protein not having a signal sequence.

* * * * *